US009750536B2

United States Patent
Lorenzini et al.

(10) Patent No.: US 9,750,536 B2
(45) Date of Patent: Sep. 5, 2017

(54) EXTERNAL FIXATION DEVICE

(71) Applicant: ORTHOFIX S.R.L., Bussolengo (IT)

(72) Inventors: Denis Lorenzini, Verona (IT); Daniele Venturini, Verona (IT)

(73) Assignee: Orthofix S.R.L., Verona (IT)

( * ) Notice: Subject to any disclaimer, the term of this patent is extended or adjusted under 35 U.S.C. 154(b) by 0 days.

(21) Appl. No.: 14/778,068

(22) PCT Filed: Mar. 11, 2014

(86) PCT No.: PCT/EP2014/000644
§ 371 (c)(1),
(2) Date: Sep. 17, 2015

(87) PCT Pub. No.: WO2014/146765
PCT Pub. Date: Sep. 25, 2014

(65) Prior Publication Data
US 2016/0192964 A1 Jul. 7, 2016

(30) Foreign Application Priority Data

Mar. 18, 2013 (IT) .......................... MI2013A000407

(51) Int. Cl.
A61B 17/00 (2006.01)
A61F 4/00 (2006.01)
(Continued)

(52) U.S. Cl.
CPC ................................ *A61B 17/6466* (2013.01)

(58) Field of Classification Search
CPC .......................................... A61B 17/58–17/66
(Continued)

(56) References Cited

U.S. PATENT DOCUMENTS 4,620,533 A * 11/1986 Mears .................. A61B 17/645
606/54
5,454,810 A * 10/1995 Pohl .................... A61B 17/6466
606/54

(Continued)

OTHER PUBLICATIONS

International Search Report, PCT/EP2014/000644, dated Jul. 21, 2014, 3 pages.

(Continued)

*Primary Examiner* — Eduardo C Robert
*Assistant Examiner* — Michelle C Eckman
(74) *Attorney, Agent, or Firm* — Baker & McKenzie LLP

(57) ABSTRACT

Fixation device for pins to be attached to an external fixation system, comprising: a first attachment or clamp comprising a first pair of opposite jaws (2) for housing at least one pin, said first pair of jaws (2) being formed by a lower jaw element (20) and an upper jaw element (30); a second attachment comprising a second pair of opposite jaws (6) that define together at least one seat for housing a rod of the external fixation system; a first clamping screw (4) for clamping the first pair of jaws (2) in order to lock in position the at least one pin, said first clamping screw (4) screwing along a screw axis (X); one of said jaw elements (30) of the first pair of jaws (2) having at least one appendix (33) on its outer edge that is shaped to interact with a corresponding recess (23) made on the other jaw element (20) of the first pair of jaws (2) so that the only possible sliding will be along the screw axis (X) of the first clamping screw (4) a second clamping screw (5) for clamping the second pair of jaws (6) onto the rod, said lower jaw element (20) of the first attachment having a projecting portion (21) with a hole (22) which the second clamping screw (5) passes through, wherein the second pair of jaws (6) is held in an open position by an elastic element (8) housed in an annular seat (Continued)

made around the hole (22) on the projecting portion (21), the second clamping screw (5) passing through the spring (8).

12 Claims, 7 Drawing Sheets

(51) Int. Cl.
*A61F 5/04* (2006.01)
*A61B 17/64* (2006.01)

(58) Field of Classification Search
USPC .................................................. 606/53–59
See application file for complete search history.

(56) References Cited

U.S. PATENT DOCUMENTS

| | | | | | |
|---|---|---|---|---|---|
| 5,624,440 | A | * | 4/1997 | Huebner | A61B 17/645 606/54 |
| 5,891,144 | A | * | 4/1999 | Mata | A61B 17/6466 606/54 |
| 5,921,985 | A | * | 7/1999 | Ross, Jr. | A61B 17/6466 606/54 |
| 6,221,072 | B1 | * | 4/2001 | Termaten | A61B 17/6483 606/54 |
| 6,652,523 | B1 | * | 11/2003 | Evrard | A61B 17/6466 606/54 |
| 7,241,074 | B2 | * | 7/2007 | Thomke | A61B 17/645 24/545 |
| 8,235,994 | B2 | * | 8/2012 | Hollawell | A61B 17/6416 606/59 |
| D683,461 | S | * | 5/2013 | Murner | D24/171 |
| D704,840 | S | * | 5/2014 | Murner | D24/171 |
| 8,808,289 | B2 | * | 8/2014 | Busch | A61B 17/6466 403/72 |
| 8,945,129 | B2 | * | 2/2015 | Dominik | A61B 17/60 606/54 |
| RE45,888 | E | * | 2/2016 | Bagnasco | |
| 2002/0026190 | A1 | * | 2/2002 | Walulik | A61B 17/645 606/57 |
| 2002/0037193 | A1 | * | 3/2002 | Gibbons | F16B 7/0433 403/344 |
| 2002/0077629 | A1 | * | 6/2002 | Hoffman | A61B 17/6466 606/59 |
| 2003/0149429 | A1 | * | 8/2003 | Ferrante | A61B 17/645 606/59 |
| 2003/0149430 | A1 | * | 8/2003 | Ferrante | A61B 17/645 606/59 |
| 2007/0038217 | A1 | * | 2/2007 | Brown | A61B 17/6466 606/57 |
| 2007/0233061 | A1 | * | 10/2007 | Lehmann | A61B 17/60 606/59 |
| 2008/0221573 | A1 | * | 9/2008 | Kumhyr | A61B 17/6458 606/59 |
| 2009/0088751 | A1 | * | 4/2009 | Mullaney | A61B 17/6466 606/59 |
| 2009/0299368 | A1 | * | 12/2009 | Bauer | A61B 17/645 606/57 |
| 2010/0298827 | A1 | * | 11/2010 | Cremer | A61B 17/6466 606/54 |
| 2011/0066151 | A1 | * | 3/2011 | Murner | A61B 17/6466 606/54 |
| 2011/0087226 | A1 | * | 4/2011 | Murner | A61B 17/6466 606/54 |
| 2011/0172664 | A1 | * | 7/2011 | Bagnasco | A61B 17/6483 606/59 |
| 2012/0004659 | A1 | * | 1/2012 | Miller | A61B 17/6466 606/54 |
| 2012/0029571 | A1 | * | 2/2012 | Schwab | A61B 17/705 606/278 |
| 2012/0089142 | A1 | * | 4/2012 | Mullaney | A61B 17/6466 606/54 |
| 2012/0095462 | A1 | * | 4/2012 | Miller | A61B 17/6466 606/59 |
| 2012/0150181 | A1 | * | 6/2012 | Dorawa | A61B 17/6466 606/59 |
| 2012/0150182 | A1 | * | 6/2012 | Dominik | A61B 17/6466 606/59 |
| 2012/0150183 | A1 | * | 6/2012 | Dorawa | A61B 17/6466 606/59 |
| 2012/0150184 | A1 | * | 6/2012 | Mullaney | A61B 17/6466 606/59 |
| 2012/0150185 | A1 | * | 6/2012 | Mullaney | A61B 17/6466 606/59 |
| 2012/0209264 | A1 | * | 8/2012 | Zandona | A61B 17/6466 606/54 |
| 2012/0209266 | A1 | * | 8/2012 | Ottoboni | A61B 17/6425 606/59 |
| 2013/0144289 | A1 | * | 6/2013 | Dorawa | A61B 17/6466 606/54 |
| 2013/0226179 | A1 | * | 8/2013 | Chreene | A61B 17/6466 606/54 |
| 2015/0119886 | A1 | * | 4/2015 | Milella, Jr. | A61B 17/6466 606/59 |
| 2016/0199098 | A1 | * | 7/2016 | Slagle | A61B 17/6458 606/59 |

OTHER PUBLICATIONS

Written Opinion of the International Searching Authority, PCT/EP2014/000644, dated Jul. 21, 2014, 5 pages.

\* cited by examiner

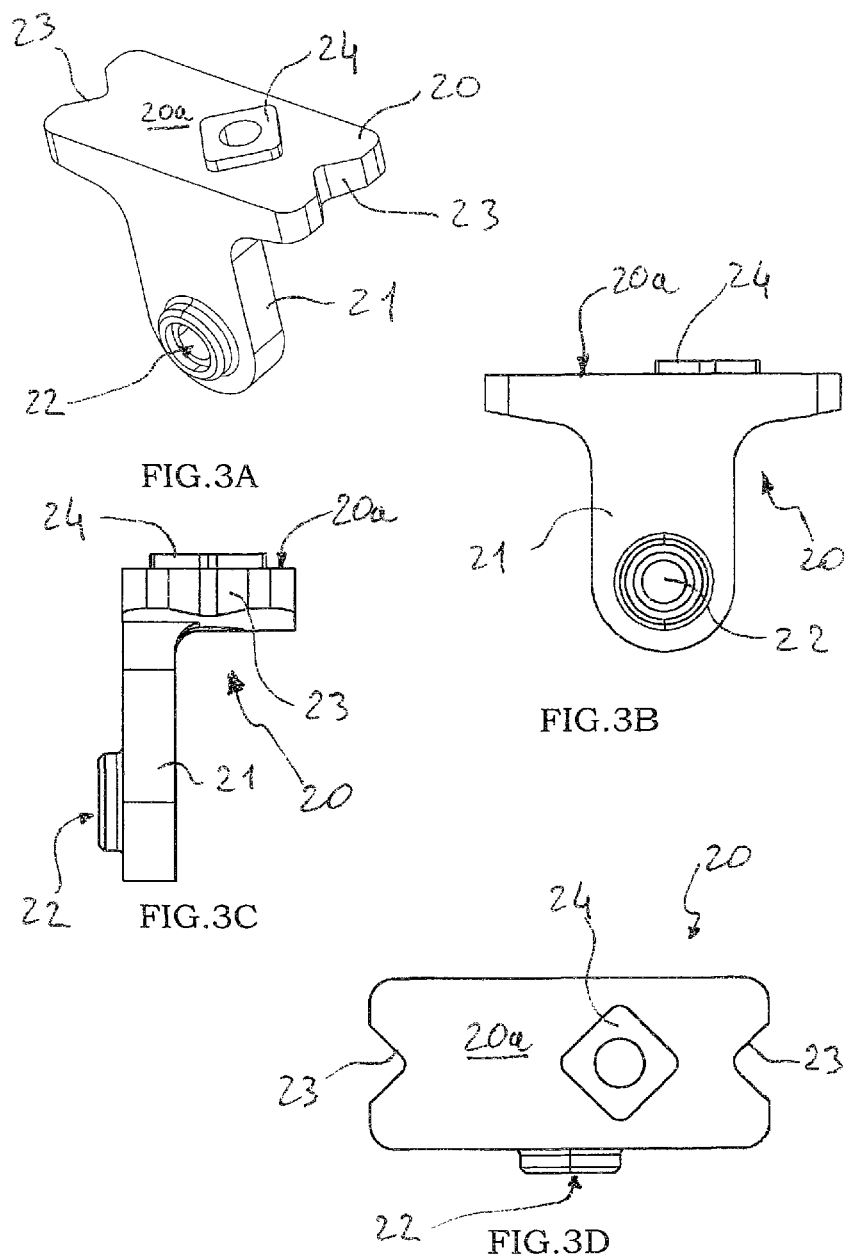

EXTERNAL FIXATION DEVICE

FIELD OF APPLICATION

The present invention applies to the field of orthopaedic surgery and it relates to a fixation device for pins.

In particular, the device is employed on external fixation systems attached to children limbs, feet and in the wrist region.

PRIOR ART

External fixation systems are widely used for treating fractured bones or for joining two or more bone fragments together. Known systems comprise pins that are inserted into bones and they employ external devices such as for example fixation clamps, fixation rods, rings etc. that allow a rigid structure to be created that is capable to keep bone fragments together in the desired position, up to a complete recovery.

These external fixation systems have the advantage to ensure a sturdiness and stability being also ensured by the use of pins that penetrate into the bones for a sufficiently long way to ensure the firm grip.

Unfortunately, the use of those known external fixation systems has several drawbacks.

In particular, known external fixation devices are constructed so as to be able to be used with pins having a determined size.

In practice, in function of the diameter of the pins to be employed there are corresponding sizes of external fixation devices.

A further constraint that prior art external fixation devices have is that they constrain the pin angular arrangement within some predetermined values and set a priori in function of the angular orientation of the seat intended to house the pin.

The technical problem underlying the present invention is, therefore, to provide a fixation device for pins to be associated to external fixation devices that allows pins to be indifferently employed, which have the desired diameter and an angular orientation not constrained a priori by the particular spatial arrangement of the pin housing seats, as it happens in prior art, in order to be able to realize extremely flexible external fixation systems, but ensuring in the meantime a sturdiness and stability that are typical of known fixation systems, within a simple and functional structural solution, and which has also the advantage of an extreme compactness, so that it can be employed in those applications requiring minimum spatial dimensions.

SUMMARY OF THE INVENTION

Said technical problem is solved by a fixation device for pins according to claim 1.

Further features and advantages will be more apparent from the following detailed description of some preferred, but not exclusive, embodiments of the present invention, with reference to the attached figures, given by way of non-limiting examples.

BRIEF DESCRIPTION OF THE DRAWINGS

FIGS. 3A-3D are different views of a lower jaw element of the device of FIGS. 1A-1D;

DETAILED DESCRIPTION

Figure 1A:
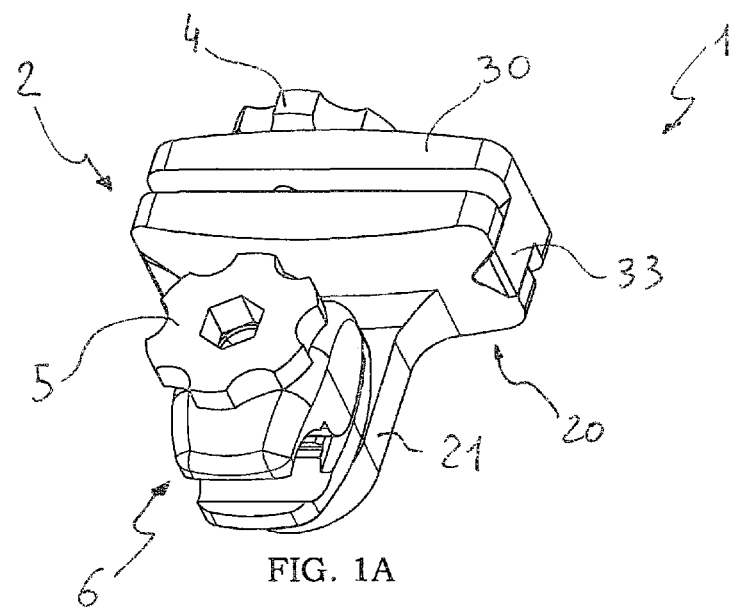
FIGS. 1A-1D are different views of a fixation device for pins according to a first embodiment of the present invention.

Referring to the attached figures, a fixation device for pins according to a first embodiment of the present invention has been identified with reference number 1.

The fixation device 1 comprising:
- a first attachment or clamp 2 comprising a first pair of opposite jaws for housing at least one pin, wherein said first pair of jaws is formed by a lower jaw element 20 and an upper jaw element 30;
- a second attachment comprising a second pair of opposite jaws 6 that define together at least one seat for housing a rod of the external fixation system;
- a first clamping screw 4 for clamping the first pair of jaws 2 in order to lock in position the at least one pin, wherein said first screw 4 screws along a screw axis X;
- a second clamping screw 5 for clamping the second pair of jaws 6 onto the rod, wherein the lower jaw element 20 has a projecting portion 21 having a hole 22 which the second clamping screw 5 passes through and in that one of the jaw elements 20, 30 of the first pair of jaws 2 has at least one appendix 33 on its outer edge that is shaped to interact with a corresponding recess 23 made on the other jaw element 30 of the first pair of jaws 2 so that the only possible sliding will be along the screw axis X of the first clamping screw 4.

In the example shown, the upper jaw 30 of the first pair of jaws 2, that acts as a lid, has two appendices 33 on two opposite outer edges. Seen in section, the two appendices 33 have a triangular shape. Evidently, the corresponding recesses 23 of the lower jaw element 20, that acts as a coupling base, have a triangular indentation too.

In substance, the two appendices 33 of the lid 30 act as lateral guides in order to prevent the lid 30 from rotating during the steps of closing-opening the clamp 2.

In this way, when screwing the first clamping screw in, the lid 30 translates vertically without rotating above the support base 20, the pins being interposed therein.

According to the present invention, both the lid 30 and the support base 20 have respective facing surfaces 30a, 20a that are level and without any recess for perfectly housing a pin.

In practice, pins are interposed between two level surfaces 20a, 30a since devoid of any groove or cavity that can house the pins themselves.

In this way pins can be freely oriented with different angles, being enabled to arrange a pair of pins with parallel, convergent or divergent orientations, and at a distance not predetermined a priori from possible pin housing cavities.

Not least, the absence of predetermined seats for housing pins allows pins with different diameters to be used. By way of example, pairs of 3 mm pins or pairs of 4 mm pins can be used with the same device 1 of the present invention.

The first and second clamping screws 4 and 5 pass respectively through the first and second pairs of jaws through a through hole.

In the example, the screw axis X of the first clamping screw 4 is arranged perpendicular to the screw axis Y of the second clamping screw 5.

Figure 1B:
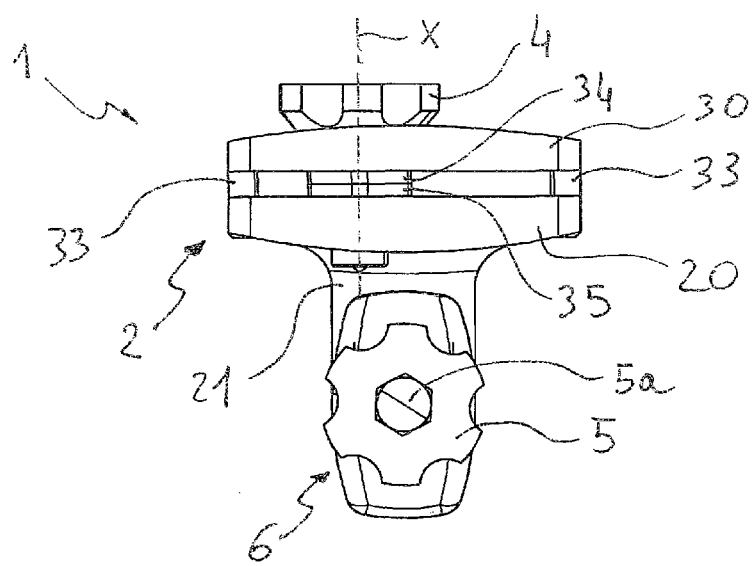
Figure 1C:
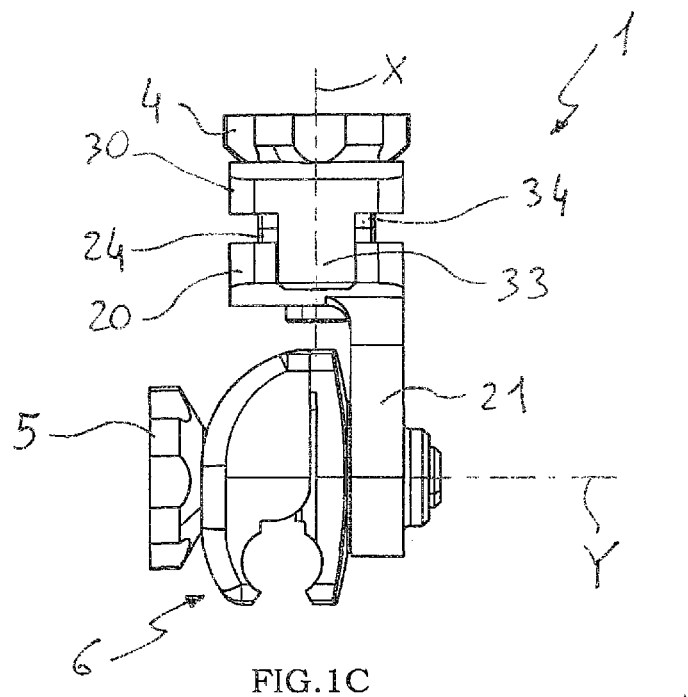
Figure 1D:
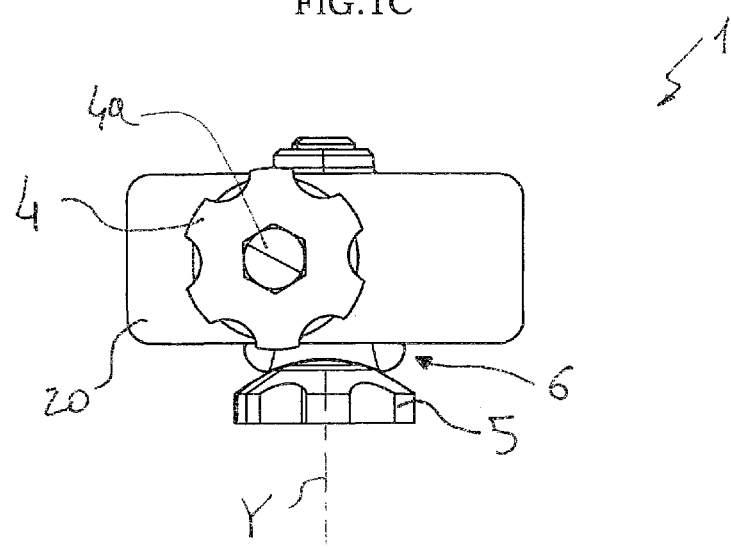
Figure 2:
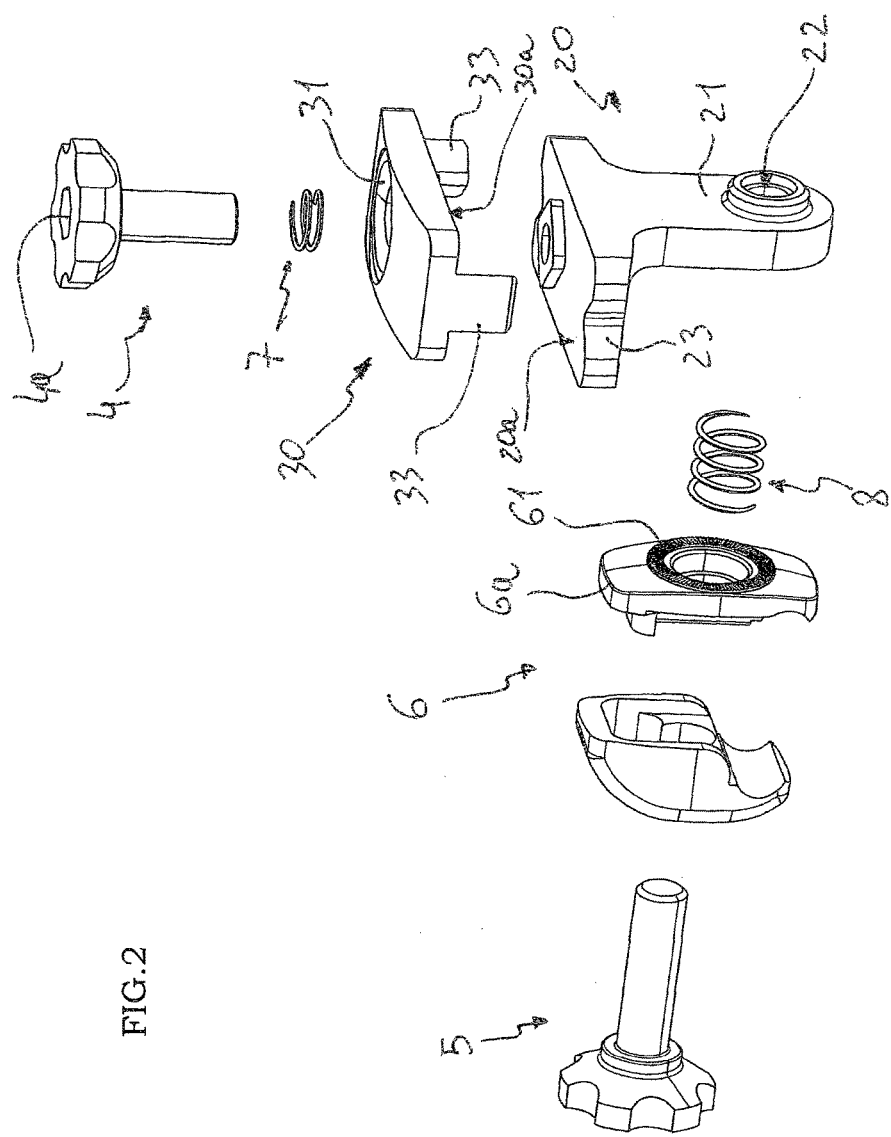
FIG. 2 is an exploded view of the device of FIGS. 1A-1D.
Figure 4A:
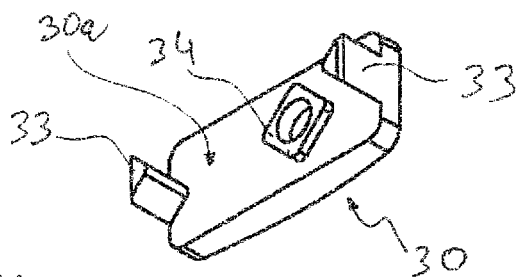
FIGS. 4A-4D are different views of an upper jaw element of the device of FIGS. 1A-1D.
Figure 4B:
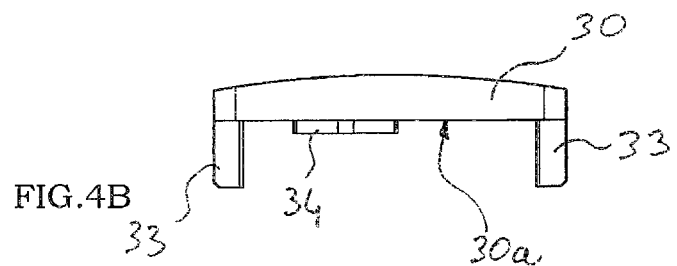
Figure 4C:
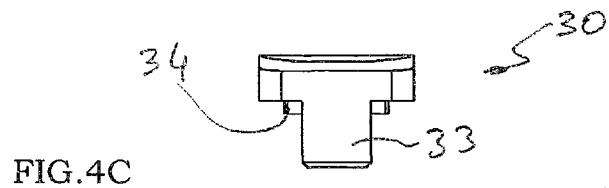
Figure 4D:
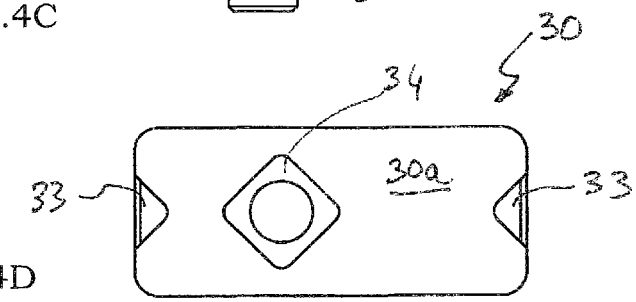
Figures 5A, 5B, 5C, 6:
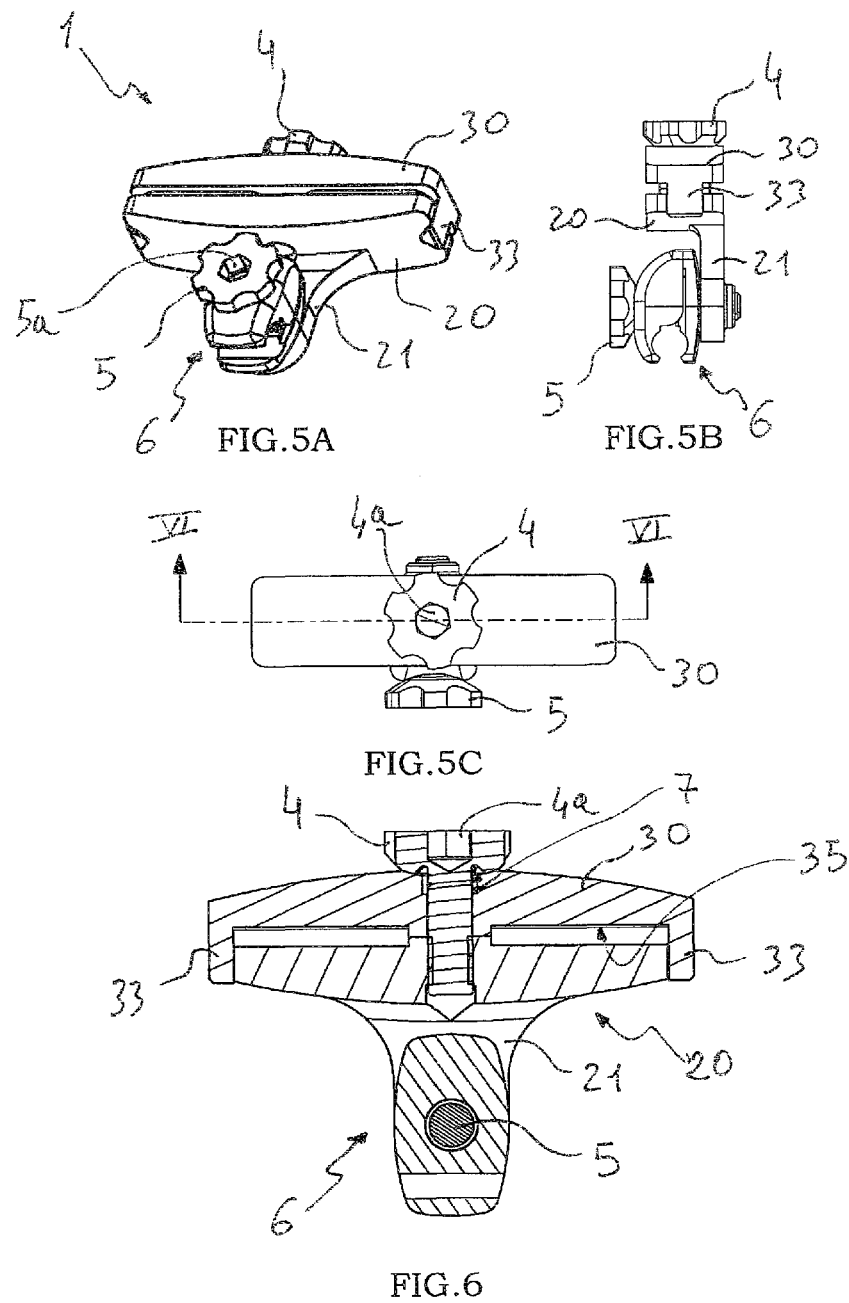
FIGS. 5A-5C are different views of a fixation device for pins according to a second embodiment of the present invention.
FIG. 6 is a sectional view taken along the plane VI-VI of FIG. 5C.
Figure 7A:
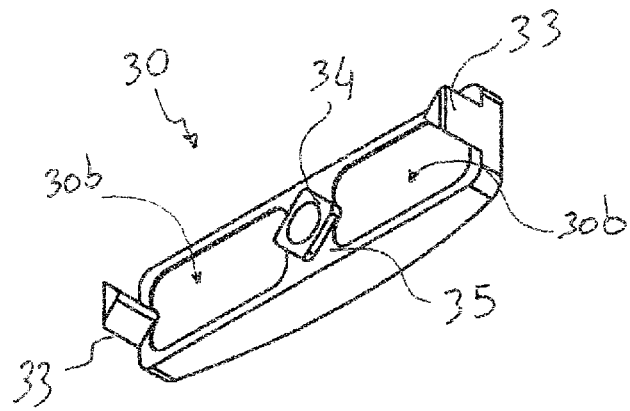
FIGS. 7A-7B are two views of an upper jaw element of the device of FIGS. 5A-5C.
Figure 7B:
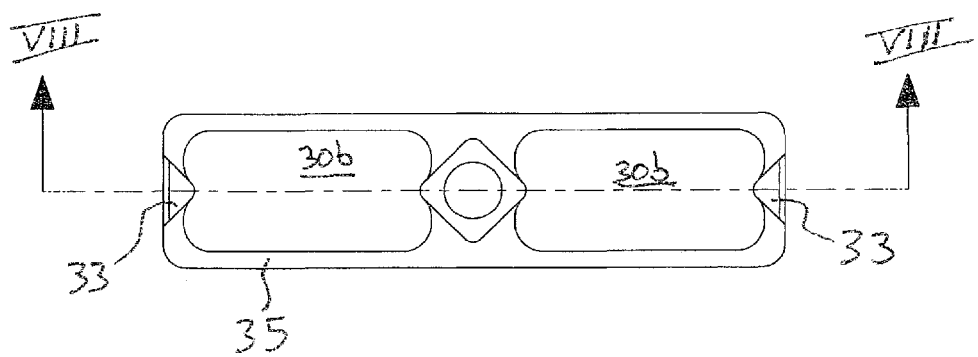
Figure 8:
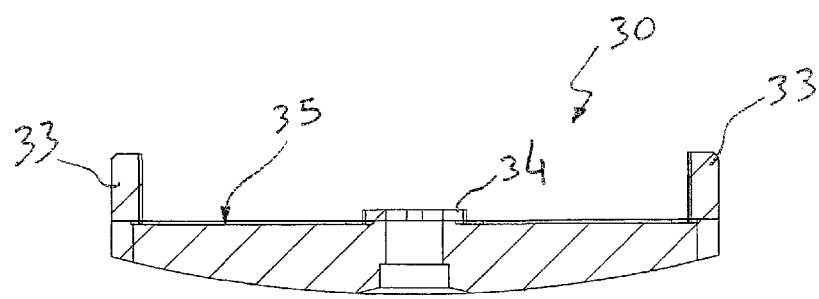
FIG. 8 is a sectional view taken along the plane VIII-VIII of FIG. 7B.

These screw axes X and Y of the two clamping screws 4 and 5 can lie on the same plane or on different planes, like in the example of FIGS. 1A-1D.

The clamp 2 is held in an open position by a first spring 7 housed in a first annular seat 31 made on the lid 30, around a hole which the first clamping screw 4 passes through.

In practice, the first spring 7 abuts between the first clamping screw 4 and the lid 30 in order to hold the lid 30 compressed onto the first screw 4 during the closing step.

On the internal surfaces 30a, 20a, where pins are placed, of the lid 30 and of the support base 20 a respective board 34, 24 with holes is provided in order to allow the first clamping screw 4 to pass through. The two boards 34, 24 abut when clamping the jaw elements 30, 20 of the first pair of jaws 2 of the clamp.

The board 24 of the support base 20 is internally threaded for the screwing of the first clamping screw 4 that, by screwing, reaches a threaded hole made on the lower jaw element 20.

The second pair of jaws 6 is held in an open position by a second spring 8 housed in a second annular seat made on the projecting portion 21 of the support base 20, in correspondence with the hole 22 which the second clamping screw 5 passes through.

The first and second springs 7 and 8 are helical springs.

The hole 22 is threaded in order to allow the second clamping screw 5 to screw in.

The second pair of jaws 6 is in practice held coupled to the projecting portion 21 of the lower jaw element 20. The element, identified with 6a in the figures, of the second pair of jaws 6 abutting against the projecting portion 21 has a knurling 61 along an annular surface around a through hole of the second clamping screw 5 in order to improve the adhesion between the second pair of jaws 6 and the projecting portion 21 of the lower jaw element 20.

The second clamping screw 5 passes through the second pair of jaws 6 and screws in the threaded hole 22 of the projecting portion 21, with the second spring 8 being placed between the second pair of jaws 6 and the projecting portion 21.

In the example, the projecting portion 21 projects from a lateral end of the lower jaw element 20 and it forms with the latter a single L-shaped piece.

In this way the second pair of jaws 6 is housed below the support base 20 in order to make the device 1 extremely compact.

The first and second clamping screws 4 and 5 are provided with a respective shaped grip head and they have in the centre a respective hexagonal impression 4a, 5a for housing a screw tool.

According to a second embodiment of the present invention, the lid 30 or upper jaw element has a support edge 35 that runs perimetrically along the internal edge.

In substance, there is a perimeter raised edge 35 projecting with respect to a level hollow 30b. In the example shown, on the internal surface of the lid 30 there are two level hollows 30b, each being surrounded by the perimeter raised edge 35, in order to have a "8"-shaped raised edge.

This allows pins to be spaced out from each other by a distance between 14 millimeters and about 45 mm.

The material forming the first pair of clamps 2 can be advantageously a radio-transparent material, such as for example peek reinforced with carbon fibres.

In the presence of a lid made of a yielding plastic material, the perimeter support edge 35 is obtained by digging the internal part of the support plane, so as to create the level hollow 35b.

By way of indication the raised support 35 of the example shown has a thickness or height of about 0.3 mm compared with the dug plane 30b and a width of about 2.5 mm.

In this way, pins are exclusively abutting on the raised support 35 that, by virtue of the fact of being yielding, undergoes a plastic deformation in the contact points with the pins, thus improving the grip of the pins onto the clamp and increasing stability.

As an alternative to making the support edge 35 in one piece with the lid, obtained by digging the internal surface of the lid 30, it is possible to attach a removable rim plate directly on the surface of the lid 30.

The rim plate would be attached to the level surface 30a of the lid and replaced when being worn.

In this latter case it is no more necessary to dig the lid 30, that could be made of a different material, since it is sufficient that the rim plate forming a raised edge on the lid has yieldingness properties.

As it can be appreciated from the above, the device according to the present invention allows the requirements and drawbacks mentioned in the introduction of the present description with reference to prior art to be met and overcome.

Obviously, in order to meet contingent and specific requirements, a person skilled in the art will be enabled to bring several modifications and changes to the above-described device, all falling however within the scope of protection of the invention, as defined by the following claims.

The invention claimed is:

1. Fixation device for pins to be attached to an external fixation system, comprising:
    a first attachment or clamp comprising a first pair of opposite jaws for housing at least one pin, said first pair of jaws being formed by a lower jaw element and an upper jaw element;
    a second attachment comprising a second pair of opposite jaws that define together at least one seat for housing a rod of the external fixation system;
    a first clamping screw for clamping the first pair of jaws in order to lock in position the at least one pin, said first clamping screw screwing along a screw axis; one of said jaw elements of the first pair of jaws having at least one appendix on its outer edge that is shaped to interact with a corresponding recess made on the other jaw element of the first pair of jaws so that the only possible sliding will be along the screw axis of the first clamping screw
    a second clamping screw for clamping the second pair of jaws onto the rod, said lower jaw element of the first attachment having a projecting portion with a hole which the second clamping screw passes through,
    wherein the second pair of jaws is held in an open position by a resilient element housed in an annular seat made around the hole on the projecting portion, the second clamping screw passing through the spring.

2. Fixation device according to claim 1, wherein said resilient element is a spring.

3. Fixation device according to claim 1, wherein said lower jaw element and said upper jaw element have respective facing surfaces that are level and without any recess for housing a pin.

4. Fixation device according to claim 1, wherein the screw axis of the first clamping screw is arranged perpendicular to the screw axis of the second clamping screw.

5. Fixation device according to claim 1, wherein between the first clamping screw and the first pair of jaws a further spring is housed in a further seat, and with the first clamping screw passing through said further seat.

6. Fixation device according to claim 1, wherein said projecting portion projects from a lateral end of the lower jaw element which it forms a single piece with.

7. Fixation device according to claim 1, wherein said upper jaw element has a pair of opposite appendices that slidingly interact with a corresponding pair of indentations made on the opposite edges of the lower jaw element.

8. Fixation device according to claim 1, wherein at least one of said lower jaw element and said upper jaw element of the first pair of jaws has a raised support that runs perimetrically along the internal edge of the corresponding jaw element, said raised support being made of a yielding material.

9. Fixation device according to claim 8, wherein said raised support is obtained through the application of a removable plate.

10. Fixation device according to claim 9, wherein said plate has radio transparency properties.

11. Fixation device according to claim 8, wherein said raised support is integrally formed with the jaw in one piece.

12. Fixation device according to claim 1, wherein the hole is threaded in order to allow the second clamping screw to screw in.

* * * * *